United States Patent [19]

Ginsburg et al.

[11] Patent Number: 4,754,752

[45] Date of Patent: Jul. 5, 1988

[54] VASCULAR CATHETER

[76] Inventors: Robert Ginsburg, 2489 Alpine Rd., Menlo Park, Calif. 94025; David F. Profitt, 1154 Madison, Santa Clara, Calif. 95050

[21] Appl. No.: 79,076

[22] Filed: Jul. 27, 1987

Related U.S. Application Data

[63] Continuation-in-part of Ser. No. 891,432, Jul. 28, 1986, abandoned.

[51] Int. Cl.$^4$ ............................................. A61B 17/36
[52] U.S. Cl. ............................. 128/303.12; 128/344; 128/401; 604/113
[58] Field of Search .................. 128/303.12, 344, 401, 128/6; 604/113–114

[56] References Cited

U.S. PATENT DOCUMENTS 4,470,407  9/1984  Hussein .................................. 128/6

OTHER PUBLICATIONS

Hiehle, Jr. et al., (1985), Am. J. Cardiol., 15:953–957.
Sanborn et al., (1985), J. Am. Coll. Cardiol., 5:934–938.

Primary Examiner—C. Fred Rosenbaum
Assistant Examiner—Gene B. Kartchner
Attorney, Agent, or Firm—Townsend & Townsend

[57] ABSTRACT

An improved balloon-tipped catheter includes means for convectively heating the inflation medium within the balloon during dilation. In the preferred embodiment, the convective heat is provided by a radiant heating block which is attached to a laser light source through an optical waveguide extending the length of the catheter. The convectively heated balloon promotes restoration and healing of the arterial wall in the region of stenosis, which region normally suffers from cracking, tearing, and stretching. It has been found that damage to the arterial wall can sometimes result in abrupt closure of the artery and frequent restenosis in the same region.

14 Claims, 3 Drawing Sheets

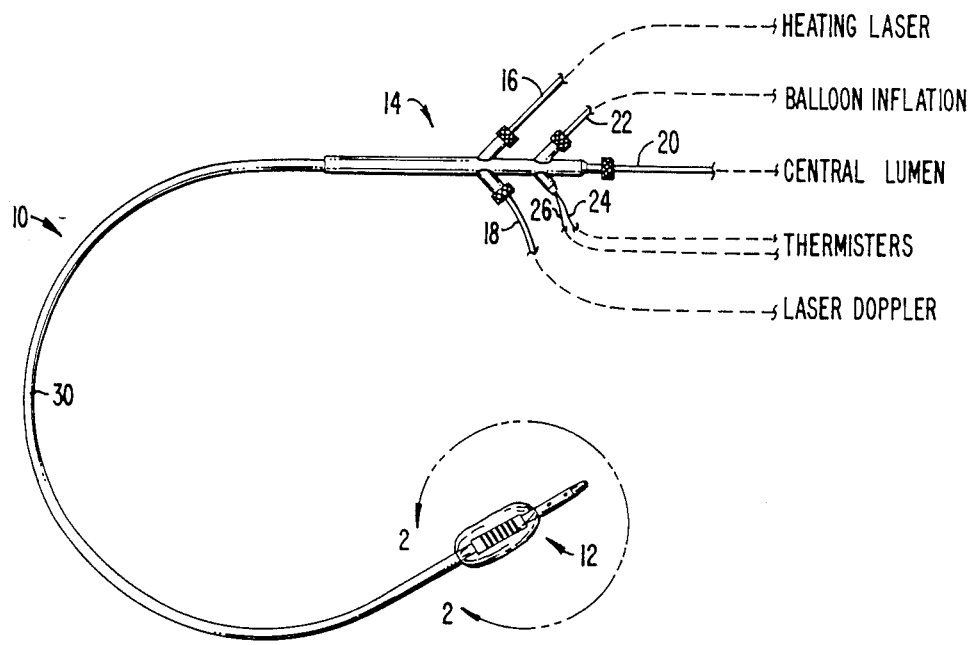
FIG.—1.
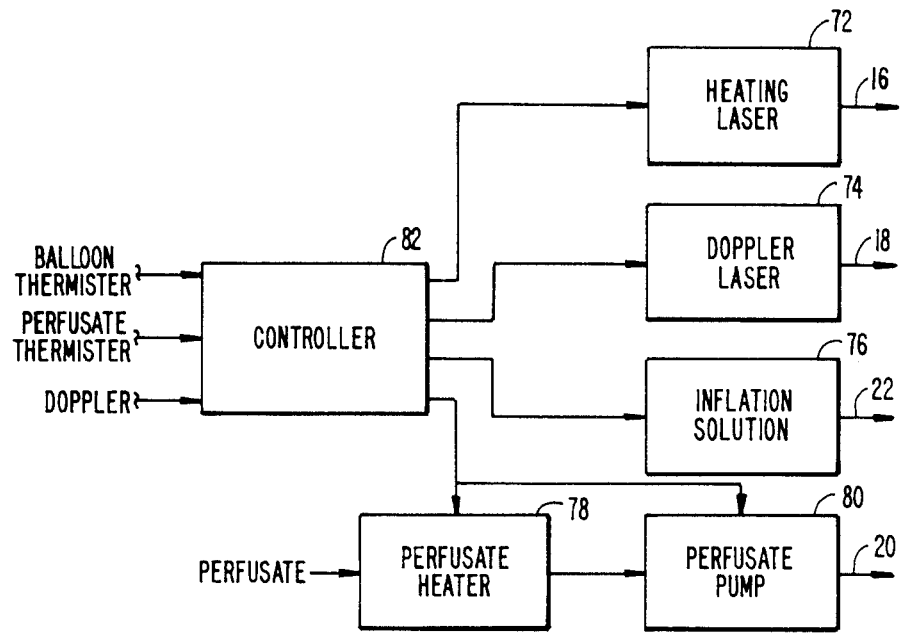
FIG.—5.

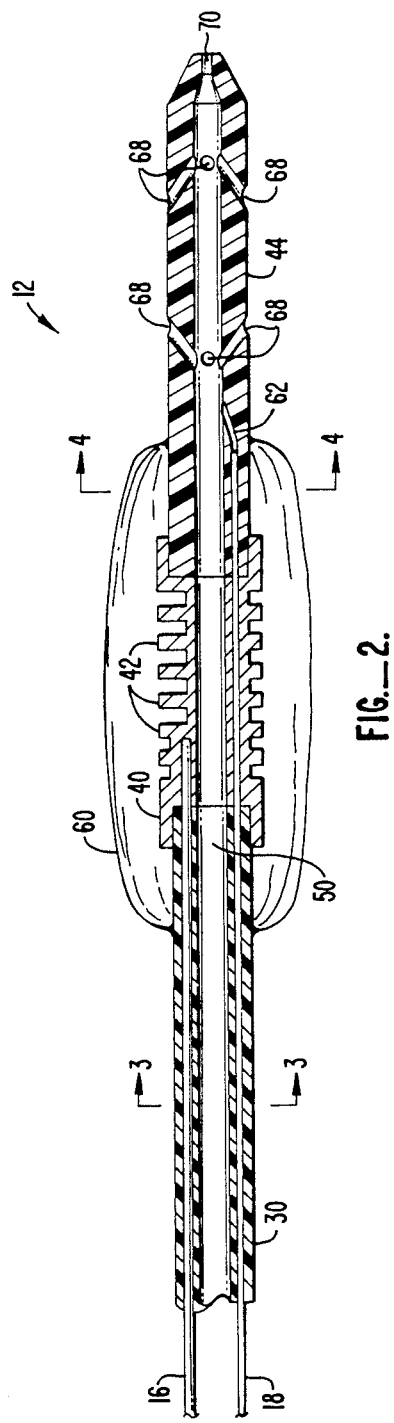
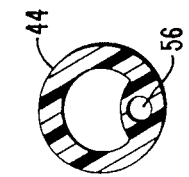
FIG._4.
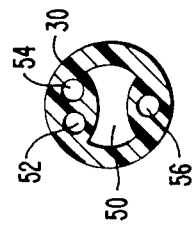
FIG._3.
FIG._2.

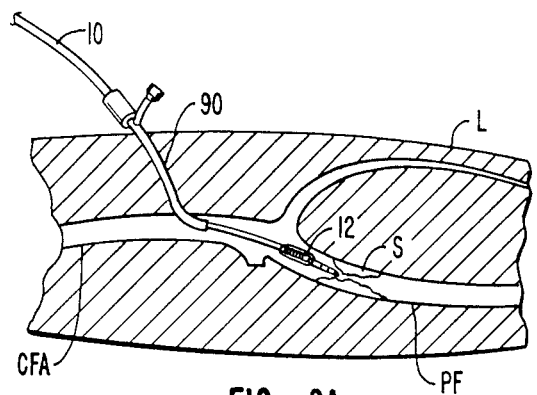
FIG._6A.
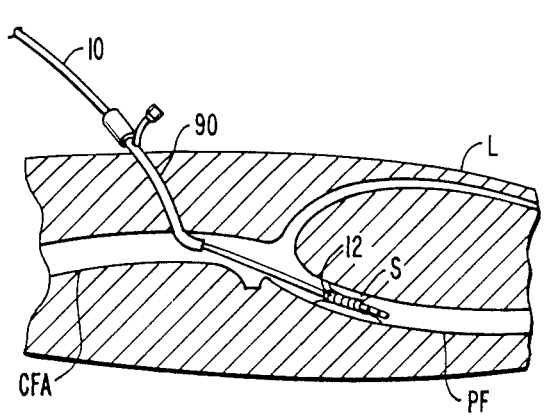
FIG._6B.
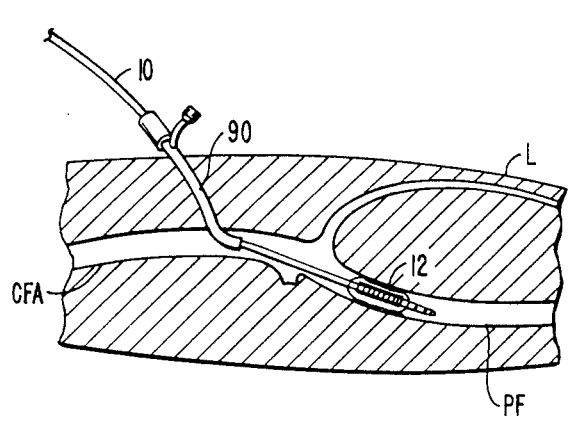
FIG._6C.

VASCULAR CATHETER

This application is a continuation-in-part of application Ser. No. 891,432, filed July 28, 1986 now abandoned.

BACKGROUND OF THE INVENTION

1. Field of the Invention

The present invention relates generally to balloon angioplasty for dilating obstructed blood vessels, and more particularly to an improved balloon-tipped catheter which provides for convectively heating a gas volume within the balloon to promote healing and sealing of damage which may occur to the interior wall of the vessel.

Balloon angioplasty was first described by Andreas Grüntzig in 1977. Dr. Grüntzig employed a balloon-tipped flexible catheter to percutaneously dilate a region of stenosis within the coronary artery of a patient with atherosclerotic coronary artery disease. Since the original work, the use of percutaneous balloon angioplasty has become widespread, with treatment of occluded peripheral blood vessels as well as coronary arteries.

Conventional balloon angioplasty compresses the plaque outwardly into the vessel wall. Such outward compression results in stress on the vessel wall, often causing cracking, tearing and stretching of the wall. In some cases, after the balloon catheter is removed, torn plaque and tissue become dislodged from the vessel wall resulting in abrupt reclosure of the vessel. Even when such abrupt reclosure does not occur, it is thought that the irregular inner surface of the vessel wall (which results from the cracking and tearing) may contribute to restenosis at the same location within the vessel. For these reasons, it would be desirable to provide a method for sealing the torn tissue and plaque to the vessel wall to provide a smooth interior surface which will not be subject to reclosure or restenosis.

One approach for promoting the healing of blood vessels damaged by balloon angioplasty has been proposed by Dr. Richard Spears and his colleagues at the Beth Israel Hospital, Harvard Medical School, Boston, Massachusetts. They proposed the use of dispersed laser radiation to promote healing and sealing of the injured vessel wall. Specifically, their technique requires that a dispersion lens be placed inside the dilation balloon, and that a Nd-YAG laser be connected to the lens by a fiber optic waveguide extending the length of the catheter. While the balloon is dilated, the laser source is activated, resulting in direct irradiation of the interior wall of the blood vessel through the balloon wall.

While Dr. Spears' technique offers many advantages, it also suffers from certain drawbacks. First, the optics required to disperse the laser radiation are only effective over relatively short distances on the order of about 10 mm. Since the length of the angioplasty balloon can be as much as 10 cm (in the case of some peripheral vessels), it becomes impractical to treat the entire length of a damaged vessel wall in a single step. Second, the outer surface of the dilation balloon is covered with blood and often becomes clouded and opaque as the balloon is inserted in the vessel and dilated to expand the stenosed region. Such obscuring of the surface can limit the transmission of the laser radiation through the balloon wall, reducing or preventing healing of the vessel wall. Third, it appears that the laser radiation, which is of a relatively high energy, has an effect on the nature of the interior of the vessel wall. The long term significance of such effects are not yet known.

For the above reasons, it would be desirable to provide methods and apparatus for promoting the healing and restoration of the interior wall of blood vessels damaged by balloon angioplasty. In particular, it would be desirable to provide such methods where the entire length of the vessel contacted by the balloon can be treated in a single step, where the treatment is unaffected by occlusion and obscuring of the outer surface of the angioplasty balloon, and where treatment does not degrade or otherwise affect the nature of the tissue on the interior of the vessel wall.

2. Description of the Prior Art

The basic technique of balloon angioplasty is taught in U.S. Pat. No. 4,195,637 to Grüntzig et al. Certain aspects of the use of Nd-YAG laser radiation to promote healing and sealing of injured blood vessel walls, as described hereinabove, are set forth in Hiehle, Jr., et al. (1985) Am. J. Cardiol. 15:953-957. U.S. Pat. No. 4,470,407 to Hussein discloses an endoscopic device having a laser beam terminating inside a balloon. The laser beam, which is directed through the wall of the balloon, is intended to illuminate and treat the interior of the wall of the vessel. The exact nature of the treatment is not made clear. Sanborn et al. (1985) J. Am. Coll. Cardiol. 5:934-938 discloses the use of a laser-heated metallic cap on a fiber optic tube, where the heated cap is used to destroy stenotic obstructions in blood vessels.

SUMMARY OF THE INVENTION

Apparatus and methods are provided for performing balloon angioplasty under conditions which promote restoration and healing of the treated region of the blood vessel. An improved balloon-tipped catheter includes means for convectively heating the volume inside the inflated balloon as the balloon is dilating the stenosis within the artery. The resulting convective heat transfer to the interior artery wall seals the plaque and endothelium to the intima of the vessel without the tissue denaturation which accompanies the use of direct laser irradiation. Moreover, the area of convective heating is not limited, and even very long balloons on the order of 10 cm or longer may be heated, allowing treatment of very large areas of stenosis. Finally, convective heat transfer is not impeded by occlusion on the surface of the balloon as is the case with direct laser irradiation.

In the preferred embodiment, the catheter comprises a flexible tube having an inflatable balloon at one end. A radiant heating block, typically a metal block having heat transfer fins, is mounted within the balloon, and a means for heating the block is provided. Conveniently, the block may be heated by a fiber optic waveguide which extends the length of the catheter and is connected at one end to an external laser light source. Other heating means, such as electrical resistance heaters, may also find use.

According to a second aspect of the present invention, a means is provided on the catheter forward of the balloon for injecting a plurality of perfusate streams into the blood vessel being treated. At least some of the streams will be directed at angles which are oblique to the axis of the catheter. Such oblique perfusate streams are particularly effective at loosening and clearing adhering platelets and clots prior to dilation of the stenosed region.

In operation, the catheter is inserted into the stenosed blood vessel by conventional techniques, typically employing a guiding catheter or sheath and a guidewire. The catheter is initially placed adjacent to the stenosis, and a pulsatile stream of perfusate is injected to clear the stenosed region of loose clots and platelets. The catheter is then moved forward so that the deflated balloon lies within the stenosed region. After inflation of the balloon, the inflation medium, typically a highly conductive liquid, is heated for a preselected time period or periods. The balloon is then deflated, the treated area having been sealed and smoothed to lessen the chance of abrupt reclosure and restenosis.

BRIEF DESCRIPTION OF THE DRAWINGS

FIG. 1 illustrates a catheter constructed in accordance with the concept of the present invention.

FIG. 2 is a detail view of the balloon tip of the catheter, shown in section.

FIG. 3 is a sectional view taken along line 3—3 of FIG. 2.

FIG. 4 is a sectional view taken along line 4—4 of FIG. 2.

FIG. 5 is a block diagram illustrating the control system of the present invention.

FIGS. 6A-6C illustrate the method of the present invention as applied to clearing the stenosed region of the profunda femoral artery in a leg.

DESCRIPTION OF THE SPECIFIC EMBODIMENTS

Referring now to FIG. 1, a vascular catheter 10 constructed in accordance with the principles of the present invention will be described. The catheter 10 includes a balloon tip 12 at its distal end and a manifold connector 14 at its proximate end. The manifold connector 14 includes ports for optical fibers 16 and 18 for connection of heating and Doppler lasers 77 and 78, respectively, as will be described in greater detail hereinafter. The manifold 14 also has ports 20 and 22 which are connected to sources for perfusate and a balloon inflation solution, respectively. Finally, the manifold 14 includes a port 23 for thermister wires 24 and 26 which are connected to balloon and perfusate thermisters, respectively. Each of these connections will be discussed in greater detail in reference to FIG. 5, hereinbelow.

The main body of the catheter comprises an elongate flexible tube 30 extending between the connector manifold 14 and the balloon tip 12. The tube 30 may be composed of a wide variety of biologically compatible elastomers, including silicone rubber, natural rubber, polyvinylchloride, polyurethanes, polyesters, and the like. The exact dimensions of the catheter 10 will vary depending on the particular use. For peripheral arteries, the catheters 10 will generally have a length in the range from about 30 to 60 cm, while for coronary arteries, the length will generally range from about 100 to 150 cm. The diameter of the catheter will generally vary from about 1 to 2 mm, with the catheters for peripheral arteries generally being larger.

Referring now to FIG. 2, the balloon tip 12 comprises a cylindrical metal block 40 mounted at the distal end of the flexible catheter tube 30. The cylindrical block 40 will typically be composed of a heat-radiating metal, such as aluminum, copper, or brass, and will include a plurality of fins 42 formed on its outer surface to enhance heat transfer to the balloon inflation medium.

A distal tip 44 is joined to the other end of the heating block 40, and the tube 30, block 40, and distal tip 44 are generally axially aligned. The distal tip 44 will usually be composed of the same flexible material as the tube 30, and each of the tube 30, block 40 and distal tip 44 include a common central lumen 50 passing therethrough. As will be described in greater detail hereinafter, the central lumen 50 allows for delivery of perfusate from the manifold 14 to the distal tip 44 of the catheter 10.

Referring now to FIGS. 2 and 3, in addition to the central lumen 50, the flexible tube 30 includes three additional lumens 52, 54, and 56, respectively. Each of the lumens is isolated from the other, and each serves to connect a different port on the manifold 14 to the catheter tip 12. Lumen 52 is connected to the balloon inflation port 22 on manifold 14, and serves to transport the balloon inflation medium to and from the interior of balloon 60.

Lumen 54 carries the optical waveguide 16 which is attached to the laser heating source 72, as will be described in more detail hereinafter. The waveguide 16 terminates in the interior of heating block 40, so that the radiation carried by the waveguide will heat the block. Usually, the waveguide will be clad along its entire length, except at the end within the heating block so that the radiation may penetrate into the block.

Finally, lumen 56 carries the laser Doppler waveguide 18. The lumen 56 extends through the metal block 40 and through a portion of the distal tip 44, as illustrated in FIG. 2. Within the distal tip 44, the waveguide 18 is exposed to the central lumen through a lateral passage 62. In this way, the waveguide 18 can measure the flow rate of perfusate being pumped through the central lumen 50.

The balloon 60 is of conventional construction, having a length in the range from about 2 to 10 cm, and a diameter when fully inflated in the range from about 4 to 8 mm. The balloon may be constructed of the same elastomers described for the flexible tube 30 and distal tip 44.

The distal tip 44 includes a plurality of oblique perfusion ports 68, as well as an axial port 70 at its distal tip. As perfusate is pumped through the central lumen 50, it is injected in oblique or inclined streams through the port 68, as well as an axially aligned stream through the distal port 70. The angle of inclination of port 68 is not critical, although they will usually lie within the range of from about 30° to 60° relative to the axial direction through the catheter. In the preferred construction, the tip 44 will include from about 4 to 24 perfusion ports 68, usually from about 8 to 16 perfusion ports, with about half the ports directed forwardly and half directed rearwardly.

Referring now to FIG. 5, the catheter 10 will be connected to a laser heating source 72 by means of the optical waveguide 16. The laser heating source 72 suitable laser heating sources include argon lasers, Nd-Yag lasers, and the like usually having a power in the range from about 5 to 40 watts.

Control of the perfusate flow through the central lumen 50 is provided by a Doppler laser controller 74 connected to the catheter through optical waveguide 18. The use of laser Doppler flow control is well known in the art and described in detail in U.S. Pat. No. 4,538,613, the contents of which are incorporated herein by reference.

A source of inflation medium 76 is connected to the catheter by conduit 22, which in turn is connected to the interior of balloon 60 by means of the lumen 52. Suitable inflation mediums include liquids having relatively high heat transfer coefficients, including water and saline. Inflation solution will be under a pressure in the range from about 50 to 150 psi.

Perfusate, typically saline, is heated to a preselected temperature, typically in the range from about 34° to 35° C. in perfusate heater 78. The perfusate is then pumped to the catheter 10 through conduit 20 where it enters the central lumen 50. The perfusate pump provides for pulsatile flow, typically with pressure peaks in the range from about 100 to 150 mmHg. The pulse cycle will be in the range from about 20 to 100 cps.

The heating laser 72, Doppler laser 74, inflation medium source 76, and perfusate heater and pump 78 and 80, are controlled by a central controller 82, which receives input from the balloon thermister 24, perfusate thermister 26, and laser Doppler system 74. The controller 82, which is typically a microprocessor-based controller, varies the output power of the heating laser 72 in order to control the temperature of the inflation medium based on the output of the balloon thermister 24. Similarly, the controller 82 controls the perfusate flow rate by varying the output of perfusate pump 80 based on the Doppler controller 74. The perfusate heater is controlled based on the perfusate thermister 26. In this way, the various parameters of the catheter 10 may be controlled based on preselected criteria.

Referring now to FIGS. 6A–6C, use of the catheter 10 of the present invention in clearing a restriction present in the femoral artery will be described. A sheath 90 inserted into the patient's leg L into the common femoral artery CFA, according to conventional techniques such as the Seldinger technique. After administering heparin, a guidewire (not illustrated) is inserted in through the sheath 90 and guided to the region of stenosis S under fluoroscopic guidance. The catheter 10 is then inserted on the guidewire until the balloon tip 12 reaches the area immediately adjacent to the region of stenosis S. After withdrawing the guidewire, perfusate is introduced through the catheter 10 in order to remove loose platelets and clots which may be present in the region of stenosis S. The use of inclined perfusion ports 68 enhances the cleaning action of the perfusate.

After clearing the stenosed region S with the perfusate, the catheter 10 is moved forward so that the balloon 60 lies within the remaining lumen of the senoses, under fluoroscopic guidance. The heating block 40 allows fluoroscopic observation, and additional radio opaque markers may be provided as desired. Once the balloon 60 is in position, as illustrated in FIG. 6B, the source of inflation medium is activated, pressurizing the balloon with the medium to a pressure in the range from about 50 to 150 psi. The pressure dilates the region of stenosis, simultaneously causing tearing, cracking, and stretching of the surrounding arterial wall. In order to restore and rehabilitate the arterial wall, as well as seal the plaque onto the wall, the inflation medium is convectively heated by radiant heating block 40. The block 40, in turn, is heated by the laser light source 72, where the laser light is transmitted by fiber optics waveguide 16.

The degree and length of the heating will depend on the particular application. Typically, the temperature will be raised to a final temperature in the range from about 40° to 80° C., above normal body temperature, more typically from about 40° to 60° C. above body temperature. The duration of heating will typically last through the entire period of inflation, although the heat may be cycled up and down during the period. A period of inflation will typically last from about 30 to 45 seconds. Frequently, it will be desirable to disinflate the balloon in order to allow restored flow of blood through the artery. This is particularly necessary with the coronary artery, where the flow of blood may not be stopped for more than about 10 to 12 seconds without causing irreversible damage to the heart. In such cases, it may be desirable to repeat the balloon dilation and heating several times in order to affect the desired permanent dilation of the stenosed region.

Although the foregoing invention has been described in some detail by way of illustration and example for purposes of clarity of understanding, it will be obvious that certain changes and modifications may be practiced within the scope of the appended claims.

What is claimed is:

1. A catheter comprising:
   a flexible tube having distal and proximal ends, the distal end being insertable into a blood vessel;
   an inflatable balloon secured to the tube near its distal end;
   means for inflating the balloon to provide a volume of inflation medium therein; and
   means for convectively heating the inflation medium in the balloon to a temperature in the range from about 40° C. to 80° C. above normal body temperature.

2. A catheter as in claim 1, wherein the means for convectively heating the volume includes a heat radiating block located inside the balloon, and means for heating the block.

3. A catheter as in claim 2, wherein the means for heating the block is a fiber optic waveguide connectable to a laser radiation source, said fiber optic waveguide being disposed to direct said radiation at said block.

4. A catheter as in claim 1, further comprising means located at the distal end of the tube for injecting a plurality of perfusate streams, wherein at least some of said perfusate streams are oblique to the axis of the tube.

5. A catheter comprising:
   a flexible tube having distal and proximal ends and at least two isolated lumens extending from the distal end to the proximal end, wherein the distal end is insertable into a blood vessel;
   an inflatable balloon secured to the tube near its distal end, said balloon being arranged to receive an inflation medium from one of said lumens to provide a volume of inflation medium within the balloon;
   a heat radiating block secured to the tube within the inflatable balloon;
   a laser radiation source; and
   a fiber optic waveguide connected to said laser radiation source and disposed to direct radiation at the block in order to convectively heat the inflation medium inside the balloon.

6. A catheter as in claim 5, wherein the fiber optic waveguide is inserted through a third lumen extending through the tube from its proximal end to a location adjacent the heat radiating block.

7. A catheter as in claim 5, wherein the heat radiating block is a finned cylinder having a hollow axial passage, wherein the hollow passage is aligned with a first lumen in the tube.

8. A catheter as in claim 7, further comprising means located at the distal end of the tube for injecting a plurality of perfusate streams, where at least some of the perfusate streams are oblique to the axis of the tube.

9. A catheter as in claim 8, wherein the means for injecting is defined by a plurality of oblique ports passing through the wall of the tube from the first lumen to the exterior, said ports being located on the distal side of the heating block so that perfusate may be passed through the first lumen and the hollow passage to said ports.

10. A method for dilating an obstructed blood vessel, said method comprising:

inserting a balloon catheter into the blood vessel so that the balloon is proxiamte the obstruction;

inflating the balloon to dialate the obstruction, wherein the dilation may also tear the endothelium from the intima of the blood vessel;

convectively heating a volume of inflation medium within the balloon to a temperature in the range from about 40° C. to 80° C. above normal body temperature.

11. A method as in claim 10, wherein the volume is heated by directing laser light at a metal block disposed within the balloon.

12. A method as in claim 11, wherein the volume is heated for a time period in the range from about 30 to 45 seconds.

13. A method as in claim 10, wherein the blood vessel is the coronary artery.

14. A method as in claim 13, wherein the blood vessel is a peripheral artery.

* * * * *